United States Patent [19]

Soldner

[11] Patent Number: 5,546,945

[45] Date of Patent: Aug. 20, 1996

[54] METHOD AND APPARATUS FOR DISPLAYING ACOUSTIC SIGNAL TRANSIT TIMES

[75] Inventor: Richard Soldner, Herzogenaurach, Germany

[73] Assignee: Siemens Aktiengesellschaft, Munich, Germany

[21] Appl. No.: 526,741

[22] Filed: Sep. 12, 1995

[30] Foreign Application Priority Data

Sep. 14, 1994 [EP] European Pat. Off. ............ 94114459

[51] Int. Cl.⁶ ............................................ A61B 8/00
[52] U.S. Cl. ........................................ 128/661.020
[58] Field of Search ............... 128/660.010, 660.050, 128/660.060, 661.020, 661.030; 73/597, 599, 602

[56] References Cited

U.S. PATENT DOCUMENTS

| | | | |
|---|---|---|---|
| 4,075,883 | 2/1978 | Glover | 73/620 |
| 4,105,018 | 8/1978 | Greenleaf et al. | 128/661.02 X |
| 4,279,157 | 7/1981 | Schomberg et al. | 128/661.020 X |
| 4,328,707 | 5/1982 | Clement et al. | 128/660.060 X |
| 4,433,690 | 2/1984 | Green et al. | 73/642 X |
| 4,669,311 | 6/1987 | McKinnon | 128/661.02 X |

FOREIGN PATENT DOCUMENTS 0097917  1/1984  European Pat. Off. .

OTHER PUBLICATIONS

"Mass Screening of Breast Cancer by Ultrasound Transmission Technique—Theoretical Considerations," Hayakawa et al., Jap. J. of App. Phys., vol. 24 (1985) Supp. 24–1, pp. 82–83.

Primary Examiner—Francis Jaworski
Attorney, Agent, or Firm—Hill, Steadman & Simpson

[57] ABSTRACT

In a method and apparatus for displaying at least one acoustic propagation property that is present within a body part suitable for diagnosis by acoustic irradiation, ultrasound transmission signals are transmitted along scan lines into the body part by an ultrasound transducer arrangement. Ultrasound signals that have passed through the body part are acquired as transmitted sound signals with a further ultrasound transducer arrangement arranged opposite the first ultrasound transducer arrangement. Parameter values are calculated from the transmitted sound signals that characterize the acoustic propagation property along the scan lines. The parameter values are portrayed on a display dependent on the corresponding scan lines.

23 Claims, 3 Drawing Sheets

5,546,945

METHOD AND APPARATUS FOR DISPLAYING ACOUSTIC SIGNAL TRANSIT TIMES

BACKGROUND OF THE INVENTION

1. Field of the Invention

The present invention is directed to a method for displaying acoustic signal transit times that occur within a body part suitable for obtaining information therefrom by acoustic irradiation, of the type wherein ultrasound transmission signals are transmitted into the body part along scan lines by an ultrasound transducer arrangement, the ultrasound signals that have passed through the body part are acquired as transmitted acoustic signals with a further ultrasound transducer arrangement which is disposed opposite the ultrasound transducer arrangement, and wherein in acoustical signal times occurring along the scan lines are calculated from respective transmission points in time of the ultrasound signals and corresponding reception points of time of the transmitted sound signals.

The invention is likewise directed to an apparatus for implementing the method of the type having an ultrasound transducer arrangement for transmitting ultrasound transmission signals along scan lines into the body part, a further ultrasound transducer arrangement arranged opposite the transmitting ultrasound transducer arrangement for acquiring ultrasound signals that have passed through the body part as transmitted sound signals, a processing unit connected to the two ultrasound transducer arrangements for identifying acoustic signal transit times from the transmitted sound signals, and a display for visual presenting the results.

2. Description of the Prior Art and Related Subject Matter

In ultrasound diagnostics, body regions or body parts are scanned with ultrasound pulses for producing anatomical tomograms. The image data are thereby acquired from echo signals or reflection signals that are triggered at boundaries of adjoining regions respectively having different acoustic characteristic impedances inside the body. The characteristic impedance is the product of the density of, and the speed of sound in the tissue types. The locus coordinates for the source of the echo signals in the tomogram on the display is obtained from the chronological spacing of the echoes from the transmitted acoustic pulse and from the propagation direction of the acoustic beam, i.e. from the position of the scan line in the sectioned plane. The transmitted acoustic beam is focused as sharply as circumstances permit. The chronological spacing is calculated in ranges or distances using an average speed of sound, amounting to 1540 m/s for soft biological tissue. The boundary surfaces of different acoustic impedances that, for example, represent organ boundaries, vessel boundaries or fine internal structures, are reproduced with relatively good geometrical precision in the tomograms obtained in this way, one form thereof being referred to as B-images.

No acoustic propagation properties that are present inside the body part itself, or inside the examination region, can be derived from this type of image presentation. Such acoustic propagation properties, for example, are the speed of sound or the acoustic absorption.

Knowledge of the acoustic propagation properties, however, is of significance for clinical diagnosis. In many instances, for example, in solid tumors the speed of sound is higher than in healthy tissue. These slight differences in the speed of sound cannot be recognized in the normal image presentation. When, for example, different acoustic propagation speeds are found within a scanned section plane, this normally leads to a slight geometrical distortion in the ultrasound tomogram that cannot be recognized. No conclusion about the speed of sound along the individual scan lines can be derived from the tomogram.

There are, however, known image presentation methods that, for example, are disclosed in European Application 0 097 917 or U.S. Pat. No. 4,075,883 that can directly display the geometrical distribution of such parameters. The acoustic signal transit time and/or the absorption are thereby measured in an acoustic irradiation method. After acoustically irradiating the examination region from a suitable number of directions, the local distribution of the speed of sound or of the absorption is calculated from the measured values with methods similar to those known from computed tomography. These methods are extremely time-consuming and employ complicated algorithms. They have not been able to find acceptance in the practical clinical routine essentially for two reasons.

First, there are only few body parts, such as mammaries and gonads that are suitable for acoustic irradiation. Second, measuring errors as a consequence of refractions occur in ultrasound computed tomography that appear as image unsharpnesses in the computer tomogram.

An acoustic irradiation method of the type initially cited is known from the article by Y. Hayakawa, entitled "Mass Screening of Breast Cancer by Ultrasound Transmission Technique-Theoretical Considerations", Proceedings of the Fifth Symposium on Ultrasound Electronics, Tokyo 1984, which appeared in the Japanese Journal of Applied Physics, Vol. 24 (1985), Suppl. 24-1, pp. 82–83. A method suitable for mass screening of the breast is proposed therein wherein average speed of sound is measured and after subtraction of, for example, the speed of sound of water, the result is displayed. In practice, however, this method has not proven satisfactory.

German patent application P 43 09 596.8 (published after the priority date of the present application) discloses that regions having different speeds of sound can be recognized in the ultrasound image when a boundary surface having a precisely known geometrical decision is located behind the structure to be diagnosed. Changes in transit time can then be recognized at this "reference surface" in the form of deviations from the "normal" geometrical appearance of this boundary surface in the displayed image. The reference surface can be produced, for example, by attaching a planar reflector plate following (in the direction of sound propagation) the body part which is acoustically irradiated. A possible disadvantage of this technique is that only echo signals can be evaluated which have passed through the examination region in the forward and return directions which may result in the generation of stronger reflection echoes than arise from the reference surface. Moreover, this reference echo can be completely absent from or imperceptible in the image as a consequence of acoustic absorption, particularly because of the double acoustic propagation path and the acoustic scatter of the reflected part in the examination region.

SUMMARY OF THE INVENTION

It is an object of the present invention to provide a method and an apparatus for obtaining an image of body part or body region by acoustically irradiating the body part or region wherein sound propagation properties of the body part or body region influenced by tumorous tissue can be calculated within a relatively short examination time and can be acquired with great precision.

In a method in accordance with the principles of the present invention, this object is achieved by displaying the acoustic signal transit times in combination with displayed marks that are arranged on image lines corresponding to the scan lines; with the spacings of the marks from the origins of the image lines correspond to the acoustic signal transit times.

In an apparatus for implementation of the method, this object is achieved by connecting a display monitor, on which the invention display is presented, to a processing unit for causing the acoustic signal transit times to be displayed dependent on the scan lines.

An advantage of the inventive method and apparatus is that the body part must be completely scanned only once. By contrast to known methods, a body part capable of acoustic irradiation such as, for example, a mammary, can be completely examined in only a few seconds. The outlay is thereby comparatively low. Clinical diagnosis of solid tumors is thus enabled because the speed of sound in such tumors is usually higher than the speed of sound in healthy tissue. This causes an attenuation of the acoustic signal transit time of acoustic pulses that have passed through tumorous or tumor-affected tissue. Deviations of the acoustic signal transit times can be displayed especially well. Given an examination region having an identical, average speed of sound throughout, the position of the marks reproduces the geometrical arrangement of the ultrasound receiver. Deviations in the presentation of the marks from the geometrical arrangement of the ultrasound receiver provide indications that a deviant speed of sound is present in the examination region traversed by the ultrasound signal. Regions having a higher speed of sound shift the mark toward the transmitting ultrasound transducer arrangement; regions having a lower speed of sound shift it away from the ultrasound transducer arrangement.

The inventive method also has advantages over the aforementioned "reference plate method". The signal to be interpreted, i.e. the ultrasound signal that is passed through the body part, can be acquired with extremely high precision because this signal is significantly stronger than a reference echo selected in a B-image. The reasons for this are, first, the transmitted ultrasound signal in the inventive method and apparatus must traverse the body part only once and experiences a correspondingly low attenuation due to absorption, and second, the additional attenuation of the acoustic pulse due to an incomplete reflection (reflection attenuation) at the reference surface is eliminated. An important advantage is also in that there are no disturbing signals before the arrival of the transmitted sound signal. Noise signals due to multiple reflections in the body part or examination region always appear following the principal pulse. By comparison, a whole series of reflection echoes that may be strong under certain circumstances and that make the interpretation of the reference echo more difficult can be present preceding the reference echo in a presentation of the reference plate method similar to the B-image. As a consequence of the two-fold attenuation of the acoustic pulse due to the forward and return path, this reference echo can be completely absent under certain circumstances. In summary, the measuring precision is improved and the susceptibility to artifacts is reduced in the inventive method compared to known methods for identifying and displaying an acoustic propagation property.

An allocation to the anatomy of the examined body part is possible on the basis of display of the acoustic signal transit time dependent on the scan lines.

In an embodiment of the method and apparatus the scan lines lie in the sectional plane. Conventional and commercially available diagnostic ultrasound apparatus can thus be utilized with little additional outlay for identifying the acoustic signal transit times.

In another embodiment, the scan lines are arranged parallel to one another. This achieves optimally short acoustic irradiation paths through the body part under examination as well as permitting the acoustic signal transit time to be allocated to the scan lines with uniformly good resolution.

In an embodiment another acoustic absorption occurring along the scan lines is calculated from the amplitudes of the transmitted sound signals and is displayed as a parameter value of a further signal propagation property. It is known from the literature that solid tumors often have an increased acoustic absorption. A second diagnostic criterion is thus established. The combination of the two criteria of acoustic signal transit time and absorption enhances the reliability of the diagnosis.

In an embodiment further echo signals generated in the body part by the ultrasound transmission signals are received with the transmitting ultrasound transducer arrangement and a tomogram is produced from the echo signals and is additionally displayed on the display monitor, with the acoustic propagation properties and the tomogram being correlated with one another by means of the common or shared scan lines. A presentation that is especially easy for an examining person to interpret is achieved due to the common display of the acoustic propagation properties and the ultrasound tomogram with the common or shared scan lines. Additionally, the reliability of the diagnosis is enhanced further because a tissue region containing a tumor can be localized as warranted in the tomogram as well as from the acoustic propagation properties displayed and correspondingly allocated thereto.

In another embodiment, examination time can be saved by calculating the tomogram and the parameter values from the same acoustic pulses transmitted by the ultrasound transducer arrangement.

In an embodiment of the inventive apparatus reception surface of the further ultrasound transducer arrangement is fashioned for location-independent reception of the transmitted sound signals along all scan lines. The allocation of the parameter values to the anatomy is defined from the respective position of the scan system and from the momentary scan direction. The ultrasound receiver only supplies the measured value of the transmitted sound signal. Identifying the location of the reception is not necessary.

In an especially simple and economic embodiment further ultrasound transducer arrangement is a piezoelectric foil. Dependent on the size of the surface, such foils can have a high capacitance. In order to prevent the received signal value from becoming too small due to this high capacitance, the foil can be structured in the form of strips. Each strip is then electrically connected to its own reception amplifier or to its own inputs of a common amplifier for further-processing the output signals produced by the respective strips.

DESCRIPTION OF THE PREFERRED EMBODIMENTS

Figure 1:
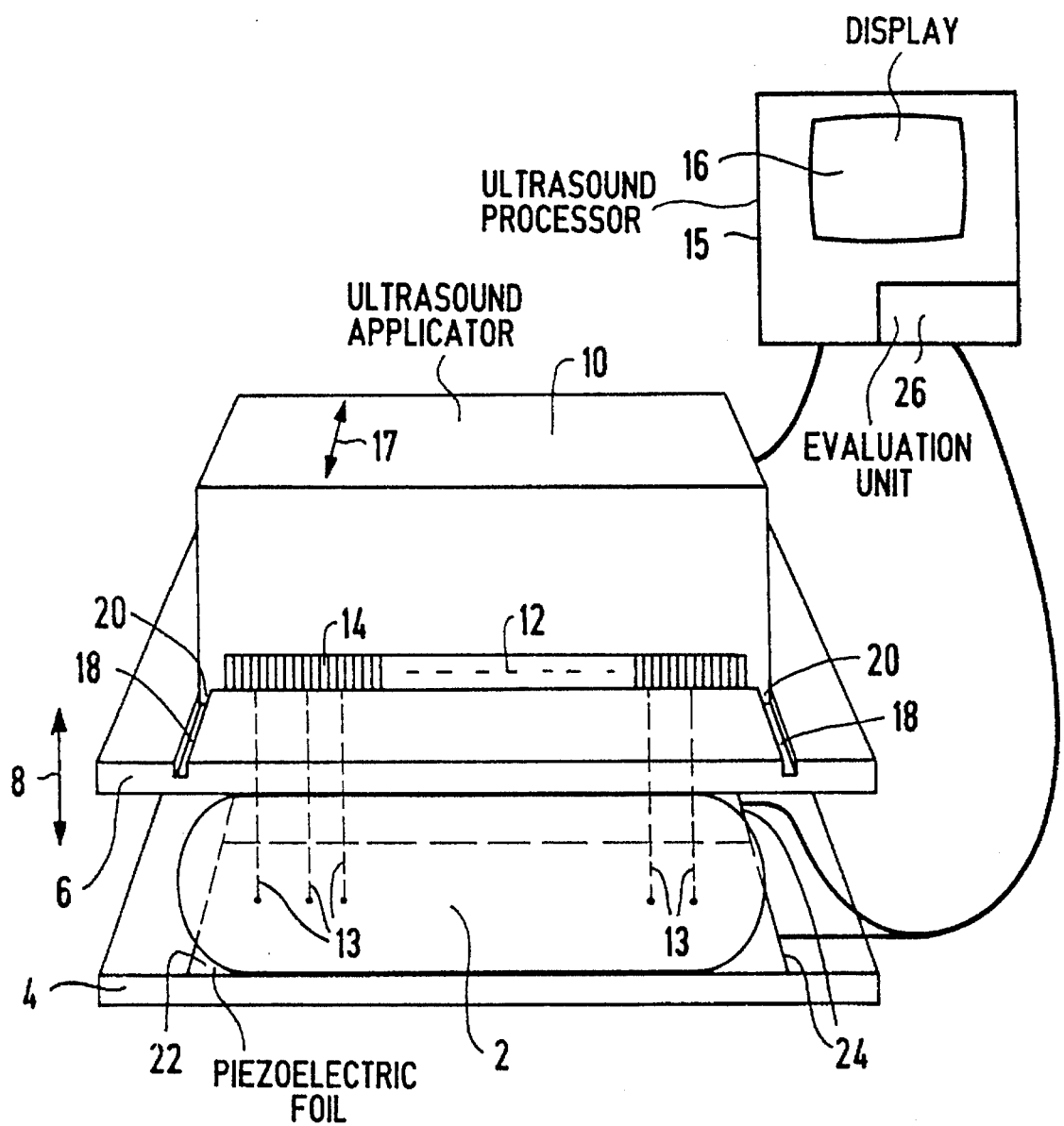
FIG. 1 is a perspective view of an apparatus constructed in accordance with the principles of the present invention for implementation the inventive method.

Acoustic propagation properties within a body part 2 suitable for diagnosis using acoustic irradiation, for example a female breast, can be calculated by means of an ultrasound scan with the apparatus shown in a perspective view in FIG. 1. During the examination, the body part 2 is fixed between two parallel compression plates 4 and 6, similar to x-ray mammography examinations. At least one compression plate, the compression plate 6 in the example of FIG. 1, is displaceable parallel to the compression plate 4. In addition to fixing the body part 2, a uniform layering of the body part 2 is thus achieved for the ultrasound examination.

In addition to the body part 2 fixing, a good acoustic coupling between the body part 2 and the compression plates 4 and 6 must be produced. This can be assured by using known coupling gels or by using an elastic container filled with a coupling fluid (not shown) that is compressed together with the body part 2.

An ultrasound applicator 10 is arranged at that side of the compression plate 6 facing away from the body part 2 and is acoustically applied thereto. The ultrasound applicator 10 has a linear array 12 of transducer elements 14 arranged side-by-side. A linear scan of the body part 2 to be examined can be implemented with this ultrasound transducer arrangement along parallel scan lines 13 lying in a section plane. For that purpose, different groups of transducer elements 14 are activated in a known way.

The ultrasound applicator 10 is connected to an ultrasound processor 15 wherein known electronic units and a display 16 are accommodated. The basic operation of such an ultrasound processor (with the exception of the modifications discussed herein) has been described in many references; for example, Erich Krestel, "Bildgebende Systeme für die medizinische Diagnostik", Second Revised and Expanded Edition, 1988, Chapter 11, "Sonographie", pp. 557–591.

In order to permit the body part 2 under examination to be completely scanned in a number of different section planes, the ultrasound applicator 10 is arranged in the compression plate 6 so as to be displaceable transversely relative to the scan direction of the linear scan, as illustrated by an arrow 17. To that end, guide channels 18 are provided in the compression plate 6, with corresponding projections 20 at the applicator housing being guided therein. The position of the ultrasound applicator 10 can be varied, for example, using a stepping motor (not shown). The position of the ultrasound applicator 10 can be identified from the control signals for the stepping motor. If, however, the position is manually varied, the position must be acquired with a position sensor whose position signal is evaluated for identifying the position of the scan plane.

Since the acoustic pulses transmitted by the transducer array 12 must pass through the compression plate 6 to the body part 2, the compression plate 6 is constructed of a material having good acoustic conduction. Moreover, the material is selected such that only slight acoustic reflections occur at the boundary surfaces. Acrylic glass, for example, is a suitable material.

In another embodiment that, however, is not shown in detail here, in a transducer mosaic is integrated into that side of the compression plate 6 facing toward the body part 2, this transducer mosaic residing in direct contact with the body part 2 during the examination and not having any mechanically moving parts. Scanning along the scan lines 13 and the selection of the individual section planes are controlled and implemented completely electronically.

Of course, a scanning with a single transducer can also be implemented, the position thereof in the surface having to be acquired or predetermined.

For the reception of the acoustic pulses that have propagated through the body part 2, a large-area piezoelectric foil 22 is arranged on that surface of the compression plate 4 facing toward the body part 2. For example, a PVD foil can be utilized as the piezoelectric foil. In order to avoid excessively high capacitance values of the foil 22 caused by the foil 22 having a large-area expanse, the foil 22 can also be structured striplike. Each foil element 24 is then connected to its own pre-amplifier in the ultrasound processor 15.

For evaluating the transmitted sound signals received by the piezoelectric foil 22, the ultrasound processor 15 includes an evaluation unit 26 that acquires the acoustic signal transit times as well as the amplitudes of the transmitted sound signals and allocates them to the scan lines 13 for display on the display 16, as set forth in greater detail below.

Figure 2:
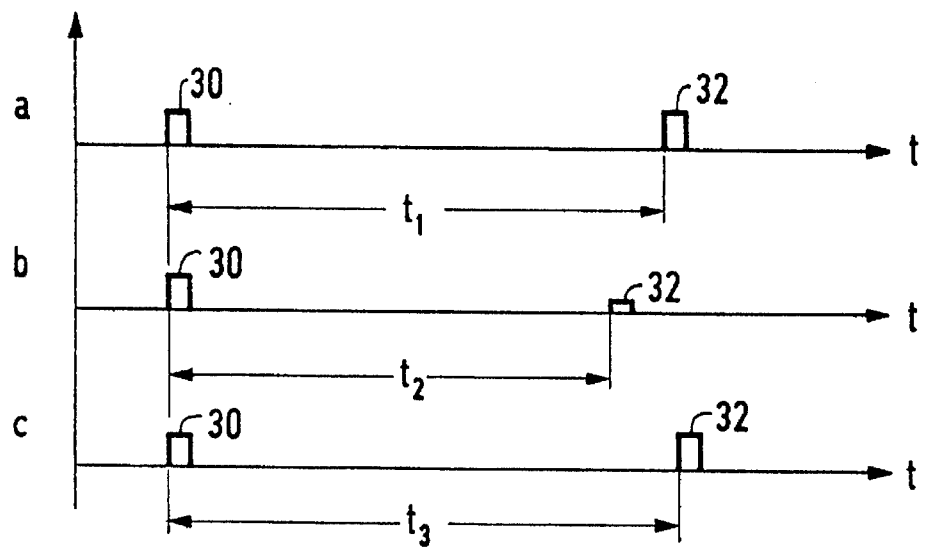
FIG. 2 is a diagram showing sound acoustic signal transit times along different scan lines.

FIG. 2 shows the chronological curve of the transmitted sound signals from which the parameter values associated with acoustic propagation properties of the body part Z along the scan lines 13 are calculated. For example, the signal curves a, b and c of three scan lines 13 from which the acoustic signal transit times are calculated first are shown. Proceeding from a transmitted ultrasound signal 30, a counter is started in every instance and is in turn stopped by the received transmitted sound signal 32. The counter readings corresponding to the acoustic signal transit times $t_1$, $t_2$ and $t_3$ are entered into in a memory together with an allocation to the corresponding scan lines.

It should be noted that the signal shapes shown in FIG. 2 are only intended to characterize the envelopes of the transmission signal and reception signal; the actual ultrasound signals are composed of high-frequency pulses in the megahertz range that are a few cycle periods long.

In the example of FIG. 2, the acoustic signal transit time $t_2$ in the diagram b is shorter than the acoustic signal transit times $t_1$ and $t_3$ of diagrams a or, respectively, c. This means that tissue having a higher speed of sound therein is located in the acoustic propagation path of the corresponding scan line 13 than is the case in the two other scan lines 13.

For calculating the absorption along the scan lines 13, the amplitudes of the envelopes of the transmitted sound signals 32 are evaluated. In FIG. 2, the transmitted sound signals 32 in diagram b have a lower amplitude than the transmitted sound signals 32 of diagrams a and c because of a higher absorption.

Figure 3:
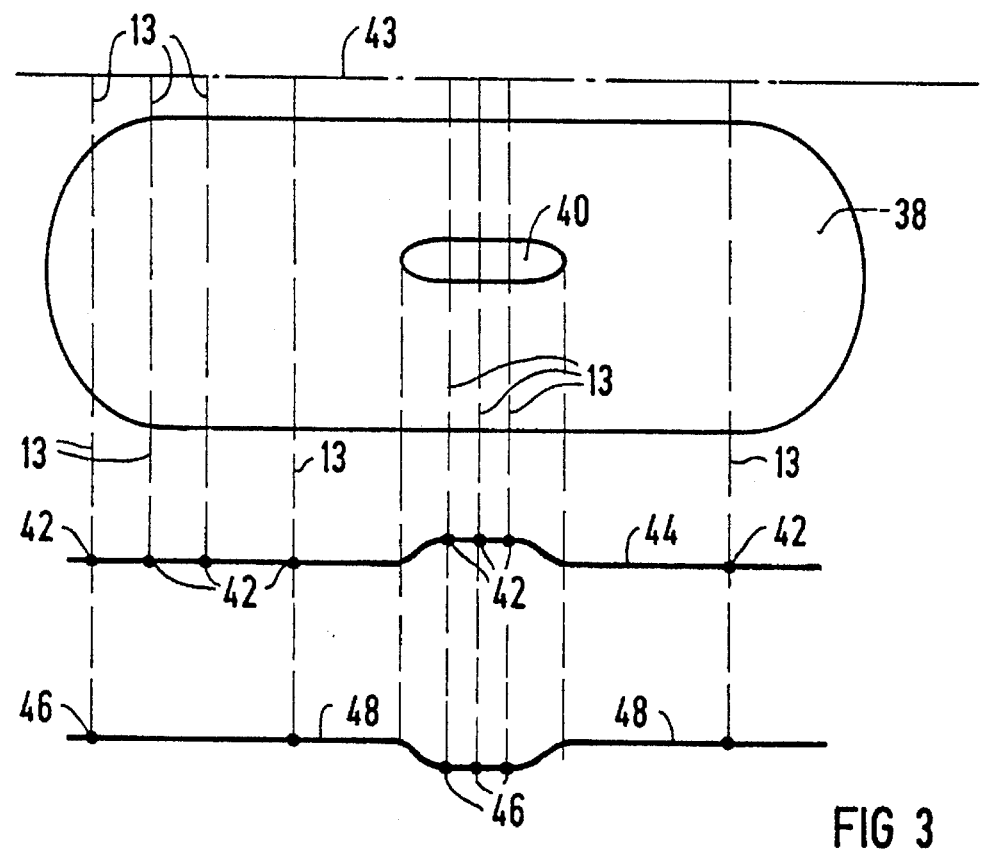
FIG. 3 illustrates the combined display of a tomogram and the parameter values of the acoustic signal transit times and the absorption associated herewith in accordance with the principles of the present invention.

FIG. 3 shows the graphic display of the information of a section plane acquired from the ultrasound scan along parallel scan lines 13 in accordance with the invention. The graphic illustration includes an ultrasound tomogram 38 wherein discontinuous changes of the acoustic impedance within the body part 2 have been rendered visible as light-colored locations in a known way. A region 40 that has a higher speed of sound therein and a higher absorption than the surrounding tissue is also present in the section plane shown with the tomogram 38. These acoustic propagation properties deviating from the average parameter values can be an indication of a tumor. The region 40 may only be slightly visible in the ultrasound tomogram 38 under certain circumstances or may be overlaid with artifacts and noise, so that it cannot be immediately recognized in the ultrasound tomogram 38 by itself.

In addition to the tomogram 38, the graphic display in FIG. 3 includes the acoustic signal transit time along the individual scan lines 13 by means of marks 42 allocated to the scan lines 13. For example, the marks 42 can appear as colored or as bright spots on the display 16, similar to boundaries of different acoustic impedances in the ultrasound tomogram 38. The illustration of the marks 42 is selected such that the distance of the marks 42 from the origin 43 of an image line which, for example, corresponds to the scan line, i.e. to the location of the transducer array 14, represents the criterion of the acoustic signal transit time. The actual distance of the marks 42 from one another is actually tighter than shown in FIG. 3, so that the individual marks 42 are smeared to form a line 44. Without the presence variations in the speed of sound, the line 44 would simulate the geometry of the ultrasound transducer arrangement 22. Given speed of sound differences in the body part 2, this displayed presentation is distorted and deviates from the profile of the ultrasound transducer arrangement 22. In a manner corresponding to the display of the acoustic signal transit times, the absorptions along the scan lines 13 are additionally shown with marks 46 that are likewise smeared to form a line 48 because of the density of the scan lines 13.

Figure 4:
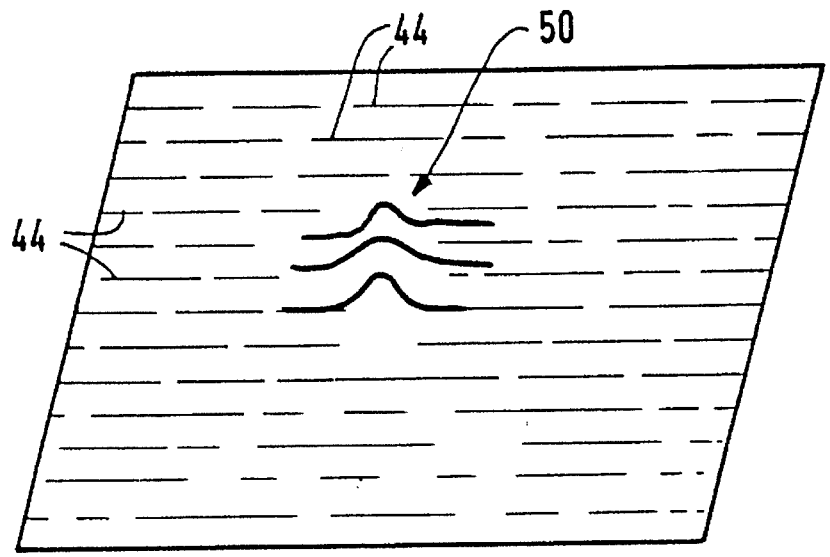
FIG. 4 illustrates the acoustic signal transit times of an entire body part in accordance with the principles of the present invention.

As an example, FIG. 4 shows what is here a perspective illustration of the marks 42 for the acoustic signal transit times, these having been calculated from all scanned section planes. Given different speeds of sound in the body part 2, portrayal resembling a mountain whose height 50 characterizes regions with higher speeds of sound arises. An indication of tumors present in the body part 2 can thus be supplied, their exact position being possibly recognizable in the associated tomogram 38.

Figure 5:
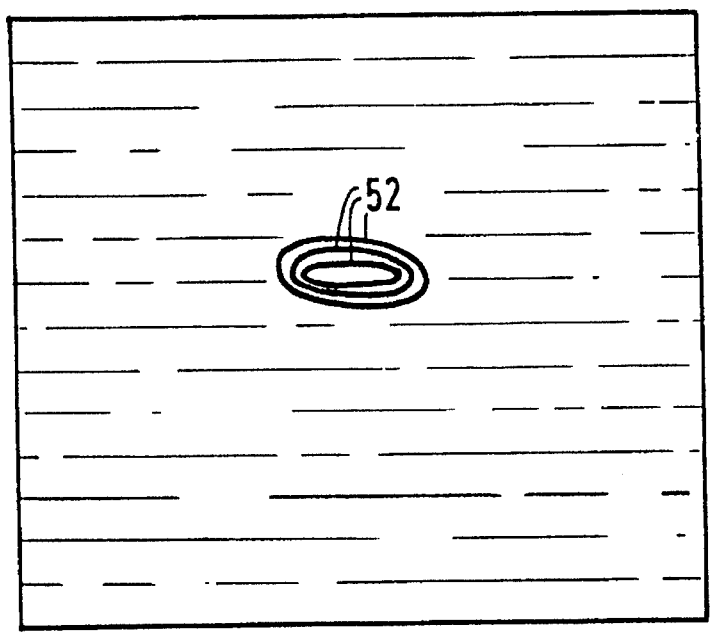
FIG. 5 illustrates a different manner of displaying the acoustic signal transit times of an entire body part in accordance with the principles of the present invention, using contour lines.

FIG. 5 shows an illustration of the acoustic signal transit times in a different manner from the display shown in FIG. 4. The acoustic signal transit times in FIG. 5 are displayed as contour lines 52, with regions between two contour lines being identified additionally if desired by coloring in the manner of illustrations of altitude regions in maps. As already discussed in connection with the illustration of FIG. 4, the section plane having higher speeds of sound therein, i.e. shorter acoustic signal transit times, can also be marked and selected.

The two illustrations of the acoustic signal transit times of FIGS. 4 and 5 can likewise be selected for overview presentations of the acoustic absorption, whereby the illustration of the acoustic signal transit time and the illustration of the acoustic absorption can ensue simultaneously on the display 16.

The illustrations of FIGS. 4 and 5 are especially advantageous for screening examinations to which ultrasound tomograms 38 are only allocated when suspicious regions having increased speed of sound therein or increased acoustic absorption have been recognized. The ultrasound tomograms 38 can already have been prepared in the ultrasound scanning for identifying the acoustic propagation properties and can be retrieved as needed from a memory.

Although modifications and changes may be suggested by those skilled in the art, it is the intention of the inventors to embody within the patent warranted hereon all changes and modifications as reasonably and properly come within the scope of their contribution to the art.

I claim as our invention:

1. A method for displaying acoustic transit times comprising the steps of:

transmitting ultrasound signals, at respective transmission points in time, into an examination subject from one side of said examination subject along a plurality of respective scan lines;

receiving said ultrasound signals at an opposite side of said examination subject at respective reception points in time after said ultrasound signals have passed through said examination subject;

calculating a transit time in said examination subject for each ultrasound signal between its transmission point in time and its reception point in time; and presenting a display of said transit times respectively arranged on a plurality of image lines respectively corresponding to said scan lines, each image line having an origin, by disposing visible marks on the respective image lines at a spacing from the origin of each image line corresponding to the transit time for the ultrasound signal transmitted along the scan line to which the image line corresponds.

2. A method as claimed in claim 1 wherein the step of transmitting said ultrasound signals comprises transmitting ultrasound signals along scan lines comprising a section plane of said examination subject.

3. A method as claimed in claim 1 wherein the step of transmitting ultrasound signals comprises transmitting ultrasound signals along scan lines comprising a plurality of section planes, each section plane having a known position.

4. A method as claimed in claim 1 wherein the step of transmitting ultrasound signals comprises transmitting ultrasound signals along parallel scan lines.

5. A method as claimed in claim 1 comprising the additional step of fixing a position of said examination subject during transmitting and receiving of said ultrasound signals.

6. A method as claimed in claim 5 wherein the step of fixing the position of said examination subject comprises fixing said examination subject between parallel compression plates.

7. A method as claimed in claim 1 wherein each ultrasound signal has an amplitude associated therewith, and comprising the additional steps of:

calculating an acoustic absorption of each ultrasound signal in said examination subject along each scan line; and displaying the acoustic absorption for each ultrasound signal together with said transit times.

8. A method as claimed in claim 1 wherein the step of transmitting ultrasound signals is undertaken in a first ultrasound transducer arrangement and the step of receiving said ultrasound signals is undertaken in a second ultrasound transducer arrangement, and comprising the additional step of:

receiving echo signals generated by the examination subject, including the substeps of:

generating ultrasound echo signals in said examination subject;

receiving said ultrasound echo signals from said examination subject with the first ultrasound transducer arrangement;

producing a tomogram of said examination subject from the received echo signals; and displaying said tomogram together with the presentation of said transit lines with scan lines being shared by the displayed tomogram and the presentation of said transit times, with said transit times being allocated to said tomogram via said shared scan lines.

9. A method as claimed in claim 8 wherein the substep of generating said ultrasound echo signals in said step of receiving echo signals is undertaken by transmitting ultrasound signals by said first ultrasound transducer arrangement so that the same ultrasound signals are transmitted through said examination subject for said step of receiving at said opposite side as are used in the step of generating said ultrasound echo signals.

10. A method as claimed in claim 8 wherein each ultrasound signal has an amplitude, and comprising the additional steps of:

calculating an acoustic absorption of each ultrasound signal in said examination subject from its amplitude; and displaying an acoustic absorption for each ultrasound signal on the respective scan lines allocated to said tomogram via said scan lines.

11. An apparatus for displaying acoustic transit times comprising:

means for transmitting ultrasound signals, at respective transmission points in time, into an examination subject from one side of said examination subject along a plurality of respective scan lines;

means for receiving said ultrasound signals at an opposite side of said examination subject at respective reception points in time after said ultrasound signals have passed through said examination subject;

means for calculating a transit time in said examination subject for each ultrasound signal between its transmission point in time and its reception point in time; and means for presenting a display of said transit times respectively arranged on a plurality of image lines respectively corresponding to said scan lines, each image line having an origin, and disposing visible marks on the respective image lines at a spacing from the origin of each image line corresponding to the transit time for the ultrasound signal transmitted along the scan line to which the image line corresponds.

12. An apparatus as claimed in claim 11 wherein said means for transmitting said ultrasound signals comprises means for transmitting ultrasound signals along scan lines comprising a section plane of said examination subject.

13. An apparatus as claimed in claim 11 wherein said means for transmitting ultrasound signals comprises means for transmitting ultrasound signals along scan lines comprising a plurality of section planes, each section plane having a known position.

14. An apparatus as claimed in claim 11 wherein said means for transmitting ultrasound signals comprises means for transmitting ultrasound signals along parallel scan lines.

15. An apparatus as claimed in claim 11 further comprising means for fixing a position of said examination subject during transmitting and receiving of said ultrasound signals.

16. An apparatus as claimed in claim 15 wherein said means for fixing the position of said examination subject comprises parallel compression plates.

17. An apparatus as claimed in claim 11 wherein each ultrasound signal has an amplitude associated therewith, and further comprising:

means calculating an acoustic absorption of each ultrasound signal in said examination subject along each scan line; and said means for presenting a display comprising means for displaying the acoustic absorption for each ultrasound signal together with said transit times.

18. An apparatus as claimed in claim 11 wherein said means for transmitting ultrasound signals comprises a first ultrasound transducer arrangement and said means for receiving said ultrasound signals comprises a second ultrasound transducer arrangement.

19. An apparatus as claimed in claim 18 wherein said first ultrasound transducer arrangement comprises a plurality of transducer elements disposed side-by-side.

20. An apparatus as claimed in claim 18 wherein said second ultrasound transducer arrangement comprises means for spatially independently receiving the transmitted ultrasound signals along all scan lines.

21. An apparatus as claimed in claim 18 wherein said second ultrasound transducer arrangement comprises a piezoelectric foil.

22. An apparatus as claimed in claim 11 further comprising:

means for generating ultrasound echo signals in said examination subject;

means for receiving said ultrasound echo signals;

means for producing a tomogram of said examination subject from the received echo signals;

and wherein said means for presenting a display comprises means for displaying said tomogram together with the presentation of said transit lines with scan lines being shared by the displayed tomogram and the presentation of said transit times, with said transit times being allocated to said tomogram via said shared scan lines.

23. An apparatus as claimed in claim 11 wherein each ultrasound signal has an amplitude, and further comprising:

means for calculating an acoustic absorption of each ultrasound signal in said examination subject from its amplitude; and said means for presenting a display comprising means for displaying an acoustic absorption for each ultrasound signal on the respective scan lines allocated to said tomogram via said scan lines.

* * * * *